US00RE35539E

United States Patent [19]

Bonaldo

[11] E Patent Number: Re. 35,539

[45] Reissued Date of Patent: Jun. 24, 1997

[54] DISPOSABLE BLOOD COLLECTION DEVICE

[75] Inventor: Jean M. Bonaldo, Upland, Calif.

[73] Assignee: Care Medical Devices, Inc., Ontario, Calif.

[21] Appl. No.: 351,563

[22] Filed: Dec. 7, 1994

Related U.S. Patent Documents

Reissue of:

[64] Patent No.: 5,070,885
Issued: Dec. 10, 1991
Appl. No.: 536,440
Filed: Jun. 11, 1990

U.S. Applications:

[63] Continuation of Ser. No. 160,993, Dec. 2, 1993, abandoned.

[51] Int. Cl.[6] ..... A61B 5/14

[52] U.S. Cl. ..... 128/763; 128/760; 604/403

[58] Field of Search ..... 128/760, 763, 128/764, 767; 604/403, 408, 411

[56] References Cited

U.S. PATENT DOCUMENTS

| | | | |
|---|---|---|---|
| Re. 33,952 | 6/1992 | Bonaldo . | |
| 4,212,307 | 7/1980 | Raitto | 128/763 |
| 4,213,456 | 7/1980 | Böttger | 128/763 X |
| 4,266,557 | 5/1981 | Merry | 128/763 |
| 4,573,976 | 3/1986 | Sampson et al. . | |
| 4,592,744 | 6/1986 | Jagger et al. | 128/763 X |
| 4,631,057 | 12/1986 | Mitchell . | |
| 4,842,587 | 6/1989 | Poncy . | |
| 4,900,310 | 2/1990 | Ogle . | |
| 4,927,417 | 5/1990 | Moncada et al. . | |
| 4,972,843 | 11/1990 | Broden | 128/760 |
| 5,011,479 | 4/1991 | Le et al. . | |
| 5,057,089 | 10/1991 | Greco . | |
| 5,219,333 | 6/1993 | Sagstetter et al. . | |

FOREIGN PATENT DOCUMENTS

| | | | |
|---|---|---|---|
| 0364387 | 4/1990 | European Pat. Off. | 128/763 |
| 8904141 | 5/1989 | WIPO | 128/763 |
| 9002515 | 3/1990 | WIPO | 128/763 |

*Primary Examiner*—Sam Rimell
*Attorney, Agent, or Firm*—Robert R. Thornton

[57] ABSTRACT

A blood collection device wherein a double-ended cannula is retracted within the barrel of the device for storage and disposal. The cannula is attached to the device immediately prior to use by being threaded into an aperture formed in a movable disc disposed within the barrel and rotated to a locked operating position for attachment of the cannula and use. After use, the disc is counter-rotated to permit the cannula, mounted to the disc, to be longitudinally retracted completely within the barrel to a position in which the cannula is permanently locked by stopping the disc against further movement. The disc aperture is threaded in the same direction as it is rotated to the operating position to avoid moving the disc out of the locked position during attachment of the cannula to the device.

18 Claims, 1 Drawing Sheet

DISPOSABLE BLOOD COLLECTION DEVICE

Matter enclosed in heavy brackets [ ] appears in the original patent but forms no part of this reissue specification; matter printed in italics indicates the additions made by reissue.

*This is a continuation Ser. No. 08/160,993 filed on Dec. 2, 1993, now abandoned.*

BACKGROUND OF THE INVENTION

1. Field of the Invention

This invention relates to a disposable blood collection device employing a double-ended cannula which is attached to the device preferably immediately prior to use, locked in an extended position for use, and retracted entirely within the barrel to a permanently locked position after use to protect against accidental needle sticks.

Medical devices using needles which are retained in a retracted position after the needle is used to guard against accidental sticks are well known. Such devices are shown, for example, in U.S. Pat. Nos. 4,650,468; 4,675,005; 4,692,156; and 4,507,117. Devices shown in the aforementioned patents are generally of the hypodermic syringe type, that is, a single needle point normally fixed to the end of a barrel and covered by a protective guard is utilized to inject fluids into or extract fluids from the human body. The needle point is retracted into the syringe barrel and retained therein by various means after use.

A somewhat different type of device has come into use with respect to the collection of blood samples. The device includes a double-ended cannula or needle, again is fixed to one end of the barrel and covered by a protective guard prior to use. The guard is removed and the end of the needle so uncovered is inserted into the patient's vein. A sterile evacuated container is applied to the other end within the barrel so that the pressure differential resulting thereby causes blood to be drawn from the vein into the evacuated container. When the container is filled, it is removed from the needle, thereby providing a sealed blood sample in the container. Examples of this type of device are shown in FIGS. 4–6 of U.S. Pat. No. 4,592,744 and in FIGS. 1–3 of U.S. Pat. No. 4,643,199. In each of these devices, a double-ended cannula is normally fixed to the end of the barrel so that one end extends from the barrel and is covered by a protective guard prior to use. After use, the double ended cannula is retracted within the barrel so as to be disposable without the danger of sticking personnel thereafter handling it. However, both of these devices require the user to use both hands in order to retract the needle after use, and thus are relatively complicated and time consuming in use. In addition, having the patient-inserted end of the cannula normally fixed to the end of the barrel takes up additional shipping space and requires removal of the guard prior to use.

A blood collection device having a double-ended cannula disposed in a barrel, open at one end to permit the insertion of an evacuated sample collection container therein onto one end of the double-ended cannula, and an aperture at the other barrel end to permit the extension and retraction therethrough of the other end of the double-ended cannula is shown in U.S. Pat. No. 4,774,964, entitled Blood Collection Device, issued Oct. 4, 1988. Jean A. Bonaldo, Inventor. This device has a first disc disposed within the barrel to which the double-ended cannula is fixed so as to extend to each side thereof and be axially aligned within the barrel in a shipping position in which the cannula is completely contained within the barrel prior to use. A second disc, disposed within the barrel between the first disc and the barrel open end, has an aperture axially formed therein so as to permit one end of the cannula to pass therethrough. The first disc and the second disc are connected together by flexible connectors within the barrel to permit preselected relative movement therebetween. When the second disc is moved toward the barrel closed end, the first disc is moved against the barrel closed end, so that the cannula extends out of the barrel aperture When the second disk is thereafter moved in the opposite direction, the first disc is withdrawn by the connectors from the barrel closed end in a spaced-apart relationship from the second disc to a position in which both ends of the cannula are disposed within the barrel. Locking means for locking the first disc and second disc within the barrel in this spaced-apart relationship and manual operating means operable for initiating the movement of said discs to said spaced-apart relationship in conjunction with said connectors are provided. However, this design is comparatively expensive to manufacture and assemble, by reason of the portions of its structure which use two discs connected together by the flexible connectors.

U.S. Pat. No. 4,900,310 describes a blood collection device housing a cylindrical sheath open at one end and partially closed at the other end with a closed longitudinal slot formed in the sheath. A piston, disposed in the sheath so as to be slidable between a cannula-extended position and a cannula retracted position, has a threaded axial bore adapted to receive a complementary threaded boss on a cannula so the cannula extends longitudinally through the piston bore with one end of the cannula in the sheath and the other end of the cannula extending through the partially closed end of the sheath when the piston is in the extended position. A radially extending actuator pin formed on the piston extends through the longitudinal slot so as to be manipulable with one hand to move the piston from the extended position to the retracted position to enclose the cannula within the sheath. The longitudinal slot may have suitable detent means at one or both ends to provide that the piston be lightly held in the extended position and locked in the retracted position. However, because the piston is only lightly held in the extended position, when the cannula is screwed into the piston, a possibility exists that excess force will cause the piston to retract, necessitating holding the piston in place by the actuator pin.

SUMMARY OF THE INVENTION

A blood collection according to the present invention is adapted to hold a double ended cannula in a cylindrical barrel, which is selectively openable at one end to permit insertion of an evacuated sample collection container therethrough on to one end of the double-ended cannula, with an aperture at the other barrel end to permit the extension and retraction therethrough of the other end of the double-ended cannula, the barrel having a disc disposed therewithin and adapted to have the double-ended cannula, which, in the preferred embodiment, is selectively fixed thereto by means of a bore in the piston threaded in a first direction and adapted to receive a complementary threaded boss on the cannula so as to have one end of the cannula extend to each side thereof and be axially aligned with the barrel in a disposal position in which the cannula is completely contained with in the barrel after use and so that when the disc is moved against the barrel closed end, the disc may be selectively locked by rotation in said first direction the operating position to receive the cannula in threaded engagement therewith, and when the disc thereafter unlocked by rotation in the opposite direction and moved longitudinally in the direction of the barrel open end to the disposal position, both ends of the cannula are disposed within the barrel, with locking means for locking the disc in the disposal position within the barrel, and manual operating means operable for initiating the rotary and longitudinal movement of the disc from the locked operating position to the locked disposal position.

BRIEF DESCRIPTION OF THE DRAWINGS

The blood collection device of the present invention is illustrated in the accompanying drawing, in which like numerals indicate like parts, and in which.

DETAILED DESCRIPTION OF THE INVENTION

Figure 1:
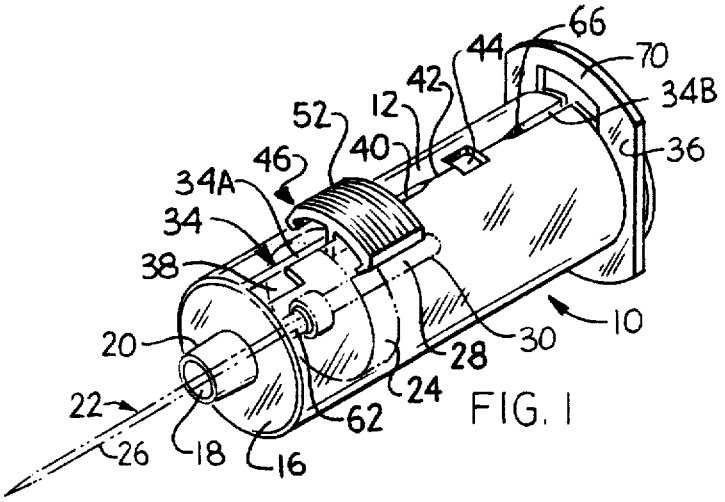
FIG. 1 is an isometric view of the blood collection device of this invention.

Referring to FIGS. 1 through 4, there is shown a blood collection device 10 which has a cylindrical barrel 12 with an open and 14 and a generally closed end 16, through which a aperture 18 is formed within a boss 20. The barrel is constructed of resilient material, such as molded medical grade polypropelyne of approximate wall thickness, typically in the one- to two-tenths inch range. A double ended cannula 22 is mounted within the barrel 12 by means of a disc 24 through which the cannula 22 extends so as to be axially aligned with the barrel. The disc 24 is mounted on the cannula 22 so that a first blood collecting needle 26 may be extended through the boss aperture 18 by movement of the disc 24 toward the closed end 16 to the disposition shown in FIG. 5 and may be retracted to the disposition shown in FIG. 6 by movement of the disc 24 away from the closed end 16.

The double ended cannula 22 has a sample transfer needle 28 which is enclosed within a latex or similar sheath 30 and is used in conventional fashion to transfer the blood from the patient through the collecting needle 26 into an evacuated sample collection container of conventional configuration (not shown), which is inserted onto the blood collecting needle 26. Such sample collection containers are well known and are sold, for example under the trademark VACUTAINER, manufactured by Becton-Dickinson Company, Rutherford, New Jersey.

The barrel 12 is of circular cross-section with a longitudinal passage 34 on its periphery terminating at the barrel closed end 16. Opposite the barrel closed end 16, at the barrel open end 14 a flange 36 is disposed, which surrounds the open end 14. The longitudinal passage 34 terminates at the barrel closed end 16 in an offset opening 38. As the longitudinal passage 34 extends toward the flange 36 from the offset opening 38, the longitudinal passage 34 terminates in a pair of oppositely disposed camming surfaces 40 which narrow the first slot portion 34A of the longitudinal passage 34 to a slit 42 formed in the barrel 12. A disposal position locking aperture 44 is disposed in the slit 42.

The disc 24 has a stem 46 at the outer periphery thereof so as to extend into longitudinal passage 34. In the disposition of the device shown in FIG. 1, the disc stem 46 is disposed between the camming surfaces 40 and the offset opening 38.

Figure 5:
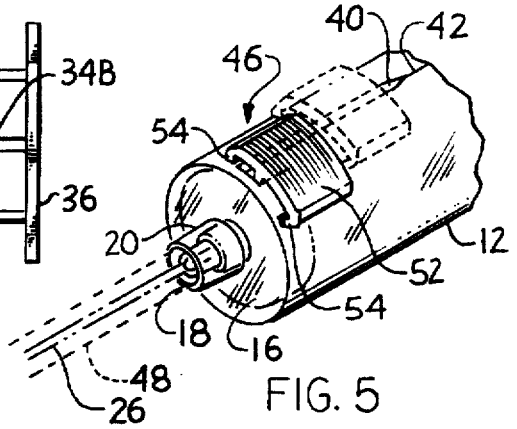
FIG. 5 is a partial isometric view of the blood collection device in its locked operating position.

Referring now to FIG. 5, there is shown an isometric view, partially broken away, of blood collection device 10 with the cannula 22 in its extended position. A solid sheath 48, shown in dotted lines, may be utilized to protect the blood collection needle 26 prior to insertion into the patient's vein, after the cannula 22 has been fixed to the blood collection device 10, as is explained hereinafter. In FIG. 5, the disc 24 has been moved laterally to abut the barrel closed end 16 so that the blood collection needle 26 extends through the aperture 18 formed in the boss 20 so as to be in its operating position. As is shown in FIG. 5, the disc 24 utilizes a blood collection needle hub 50 which extends outwardly axially from the disc 24 to seat in the aperture 18 formed in the boss 20 to provide a rigid seat for the blood collection needle 26 in the barrel 12.

The disc 24 is moved in to the position shown in FIG. 5 by movement applied manually to the disc stem 46 at a finger engagement portion 52 thereof. The disc stem 46 is disposed and locked in the offset opening 38 formed in the barrel 12 when the blood collection device 10 is in the configuration shown in FIG. 5. The disc 24 has been rotated clockwise from the position shown in FIG. 1, which position is shown in FIG. 5 in dotted lines, so as to have the disc stem 46 disposed in the offset opening 38. The stem 46 is stabilized against the barrel 12 and held in this rotated position by means of frictional engagement of a pair of small rails 54, formed on the underside of the finger engagement portion 52 of the lateral extremities thereof, with the outer surface of the barrel 12 at the edge of the offset opening 38.

Figure 6:
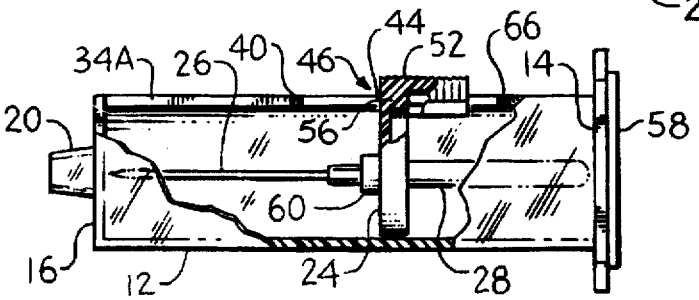
FIG. 6 is a partial side elevational view of the blood collection device in its locked disposal position.

When it is desired to retract the blood collection needle 26 from the operating position shown in FIG. 5 to the disposal position shown in FIG. 6, the disc stem 46 is rotated counterclockwise manually by means of the finger engagement portion 52 so as to align a stem portion 56 of the stem 46 with the longitudinal passage slot portion 34A. The disc 24 is then moved toward the open end 14 of the barrel by manual longitudinal pressure on the finger engagement portion 52. This longitudinal movement of the disc 24 away from the closed end 16 of the barrel 12 retracts the blood collection needle 26 into the barrel 12.

As the disc stem 46 reaches the camming surfaces 40, which are formed on the longitudinal passage 34 so as to taper inwardly toward one another, further longitudinal movement of the stem portion 56 then overrides the camming surfaces 40 to open the slit 42 and permit the stem portion 56 and so the disc 24 to approach the disposal position locking aperture 44. When the stem portion 56 enters the disposal position locking aperture 44, the camming action of the stem portion 56 with respect to the slit 42 ends, permitting the slit 42 to close so as to lock the stem 56 in the disposal position locking aperture 44. The disc 24 is thereby locked in its disposal position.

The disc 24 is thereby locked in the disc position shown in FIG. 6, in which the blood collection needle 26 is retracted within the barrel 12 and the sample transfer needle 28 is contained within the barrel 12 short of the open end 14 thereof. The blood collection device 10, having been used, is therefore in condition for disposal, with both needle points contained with the barrel 12 so that personnel involved in the disposition are protected from being stuck by either end of the double-ended cannula 22. A cap 58 is preferably attached to the barrel open end 14 by hinges 58A and then is in manually pressed onto the barrel open end 14 to close the open end so as to avoid any possibility of sticks from the sample transfer needle 28 by insertion of a finger into the barrel open end 14.

In the present invention, the cannula 22 may be molded into the disc 24. However, in the preferred embodiment, it is desirable, but not essential, to secure the double-ended cannula 22 to the disc 24 after shipping, storage and similar handling and immediately prior to actual use, in order to avoid possible contamination of the needle or accidental sticks. The blood collection device 10 is configured so that the disc 24, when disposed adjacent to the barrel closed end 16, may be locked in such an operating disposition by clockwise rotation of the stem portion 56 which is attached to the disc 24 into the closed end locking aperture 18. When so disposed, the disc 24 will be stopped by the stem portion 56 location in the aperture 18 so as to prevent the disc 24 from moving longitudinally toward the barrel open end 14 without the counter-rotation of the disc 24 in a counterclockwise direction to align the stem portion 56 with the longitudinal passage 34,. The cannula 22 can then be screwed into the disc 24 through the closed end 18 by means of a threaded aperture 60 axially formed in the disc 24 and a complementary threaded portion formed on hub 62 of the cannula 22.

Figure 2:
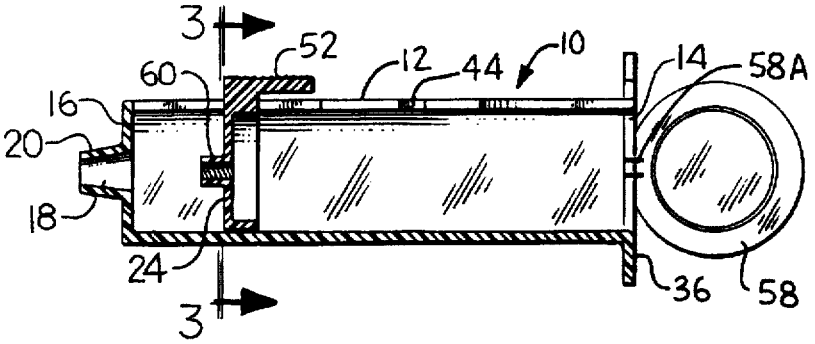
FIG. 2 is a side elevational view of the device of FIG. 1.
Figure 3:
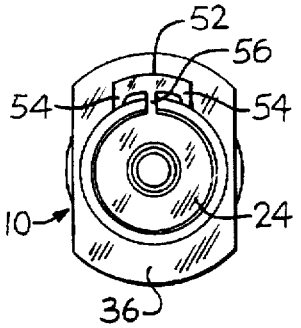
FIG. 3 is a front elevational view, partially broken away, of the blood collection device of FIG. 1 taken along lines 3—3 of FIG. 2.
Figure 4:
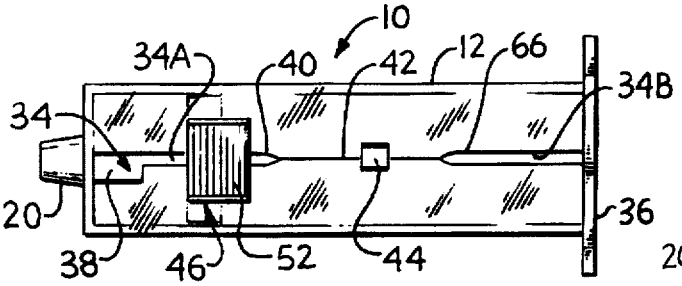
FIG. 4 is a plan view of the blood collection device in its disposition shown in FIG. 1.

As is shown in FIG. 2, the threaded aperture 60 has clockwise threads, so that when the cannula boss 62 is threaded thereinto, the torque applied in threading forces the stem portion 56 against the longitudinal wall of the offset opening 38, to guard against accidental retraction of the disc 24 where the cannula 22 is being attached thereto.

For ease of assembly of the disc 24 into the barrel 12, the longitudinal slit 42, between disposal position stop aperture 44 and the flange 36, opens through a second pair of camming surfaces 66 into a second longitudinal passage slot 34B, which passes through the flange 36 at a flange slot 70. The configuration of the flange slot 70 is complementary to the configuration of the finger engagement portions 52 of the stem 46, so as to permit passage of the finger engagement portion 52 therethrough. To assemble the device 10, other than the cannula 22, the disc 24 is inserted into the barrel open end 14 with the stem 56 aligned with the longitudinal passage slot 34B, so that the finger engagement portion 52 passes through the flange slot 70. The finger engagement portion 52 is manually urged toward the disposal position stop aperture 44 so that stem portion 56 engages the second camming surfaces 66 to open the slit 42 and permit the stem 56 to pass into the disposal position locking aperture 44, at which time the slit 42 closes, locking the stem 56 in the aperture 44. Because the barrel is made of resilient plastic material, the slit 42 between the camming surfaces 40 and the aperture 44 can be opened manually by inserting an appropriate tool of blade type configuration into the longitudinal passage 34 and rotating the tool up to ninety degrees so as to open the slit 42 and permit the stem portion 56 to pass from the disposal position locking aperture 44 through the slit 42 and through the camming surfaces 40, at which time any camming action by the stem 56 on camming surfaces 40 ends, so as to permit the slit 42 to close. The device is then ready for shipment and attachment of the cannula, as described above.

The invention claimed is:

1. A blood collection device comprising:

a cylindrical barrel formed of a resilient material and closed at one end with an axially disposed aperture formed therein so as permit the extension and retraction through said barrel aperture of one end of a double-ended cannula, said cylindrical barrel being open at the other end to permit insertion of a sample collection container into the other end of said cannula and the removal thereof therethrough;

a disc transversely disposed within the barrel and adapted to receive the double-ended cannula by the threaded engagement of threads formed on a boss on the cannula with threads formed in an aperture in the disc so that said one end of the cannula is disposed to one side of the disc and said other end of the cannula is disposed to the other side thereof, said cannula thereby being axially aligned with the barrel;

a longitudinal passage formed in the surface of said barrel so as to extend parallel to the barrel axis from immediately adjacent the barrel closed end through the barrel open end;

a stem connected to the disc within the barrel so as to extend externally of the barrel and generally transverse thereto and operable to initiate longitudinal movement of the disc relative to the barrel to an operating position adjacent barrel closed end, in which, when said cannula is fixed to said disc, one end of the cannula extends out of the barrel aperture, and in which, when the disc is moved longitudinally away from the barrel closed end to a preselected disposal position between the barrel open end and the barrel closed end, both ends of the cannula are disposed within the barrel;

locking means for locking the disc in said disposal position;

closing means selectively operable to close the open end of the barrel;

and in which said longitudinal, passage includes a slot portion adjacent the barrel closed end and terminating thereat offset opening so disposed that the disc stem can be rotated thereinto when the disc is adjacent the barrel closed end to lock the disc against longitudinal movement, and a disposal position locking aperture formed in a portion of the longitudinal passage between the barrel open end and the barrel closed end in a portion thereof comprised by a longitudinal slit, said slot portion narrowing into said slit portion by means of a first camming surface formed on the barrel between the offset opening and the locking aperture.

2. The blood collection device of claim 1, and in which the slit portion of the longitudinal passage extends from said first camming surface through said locking aperture toward said barrel open end and terminates between said locking aperture and said barrel open end in a second camming surface which opens from said slit portion into a second longitudinal slot portion formed in said longitudinal passage.

3. The blood collection device of claim 2, and including a peripheral flange formed on the barrel at the open end thereof, said flange having an aperture formed therein so as to be in communication with the second longitudinal slot portion to permit the disc stem to pass through the flange aperture into the longitudinal passage when the barrel open end is not closed by said closing means.

4. The blood collection device of any of the preceding claims, and in which the longitudinal slot offset opening is offset in the same direction as the threads in the disc aperture, whereby threading the cannula into the disc will urge the disc stem into the offset opening when the disc is adjacent the barrel closed end.

5. The blood collection device of claim 4, and in which the disc stem terminates in a finger engaging portion having a finger engaging surface extending substantially normal to the disc stem and laterally therefrom so as to be disposed externally of the barrel and generally concentrically with a portion thereof, said finger engaging surface terminating at each of its two lateral extremities in a depending rail portion which engages said barrel, whereby said finger engaging portion is stabilized against said barrel.

6. A blood collection device comprising:

a cylindrical barrel formed of a resilient material and closed at one end with an axially disposed aperture formed therein so as permit the extension and retraction through said barrel aperture of one end of a double-ended cannula, said cylindrical barrel being open at the other end to permit insertion of a sample collection container onto the other end of said cannula and the removal thereof therethrough;

a disc transversely disposed within the barrel and to which the double-ended cannula is fixed so that said one end of the cannula is disposed to one side of the disc and said other end of the cannula is disposed to the other side thereof, said cannula thereby being axially aligned with the barrel;

a longitudinal passage formed in the surface of said barrel so as to extend parallel to the barrel axis from immediately adjacent the barrel closed end through the barrel open end;

a stem connected to the disc within the barrel so as to extend externally of the barrel and generally transverse thereto and operable to initiate longitudinal movement of the disc relative to the barrel to an operating position adjacent barrel closed end, in which one end of the cannula extends out of the barrel aperture, and in which, when the disc moved longitudinally away from the barrel closed end to a pre-selected disposal position between the barrel open end and the barrel closed end, both ends of the cannula are disposed within the barrel;

locking means for locking the disc in said disposal position;

closing means selectively operable to close the open end of the barrel;

and in which said longitudinal passage includes a slot portion adjacent the barrel closed end and terminating thereat in an offset opening so disposed that the disc stem can be rotated thereinto when the disc is adjacent the barrel closed end to lock the disc against longitudinal movements, and a disposal position locking aperture formed in a portion of the longitudinal passage between the barrel open end and the barrel closed end in a portion thereof comprised by a longitudinal slit, said slot portion narrowing into said slit portion by means of a first camming surface formed on the barrel between the offset opening and the locking aperture.

7. The blood collection device of claim 6, and in which the slit portion of the longitudinal passage extends from said first camming surface through said locking aperture toward said barrel open end and terminates between said locking aperture and said barrel open end in a second camming surface which opens from said slit portion into a second longitudinal slot portion formed in said longitudinal passage.

8. The blood collection device of claim 7, and including a peripheral flange formed on the barrel at the open end thereof, said flange having an aperture formed therein so as to be in communication with the second longitudinal slot portion to permit the disc stem to pass through the flange aperture into the longitudinal passage when the barrel open end is not closed by said closing means.

9. The blood collection device of any of claims 6, 7 or 8, and in which the longitudinal slot offset opening is offset in the same direction as the threads in the disc aperture, whereby threading the cannula into the disc will urge the disc stem into the offset opening when the disc is adjacent the barrel closed end.

10. In a medical device, the combination of:

a cylindrical barrel formed of a resilient material and having a first end and a second end, said second end being open to permit insertion of a container into said second end;

disc means transversely disposed within the barrel so as normally to be positioned adjacent to said first end and having an aperture adapted to receive a cannula in axial alignment with the barrel by the threaded engagement of threads formed on a boss on the cannula with threads formed on the disc means;

a longitudinal passage formed in the peripheral surface of said barrel so as to extend parallel to the barrel axis from immediately adjacent the barrel first end through the barrel second end;

a stem connected to the disc means within the barrel so as to extend externally of the barrel and generally transverse thereto and operable to initiate longitudinal movement of the disc means relative to the barrel to an operating position adjacent barrel first end, in which, when said cannula is fixed to said disc means, one end of the cannula extends out of the barrel first end, and in which, when the disc means is moved longitudinally away from the barrel first end to a pre-selected disposal position between the barrel second end and the barrel first end, the cannula is completely disposed within the barrel; and locking means for locking the disc means in said disposal position;

and in which said longitudinal passage includes a slot portion adjacent the barrel first end and terminating in an offset opening disposed at the first end so that the disc stem can be rotated thereinto when the disc means is adjacent the barrel first end to lock the disc means against longitudinal movement, and a disposal position locking aperture formed in a portion of the longitudinal passage between the barrel second end and the barrel first end in a portion thereof comprised by a longitudinal slit, said slot portion narrowing into said slit portion by means of a first camming surface formed on the barrel between the offset opening and the locking aperture.

11. The combination of claim 10, and in which the slit portion of the longitudinal passage extends from said first camming surface through said locking aperture toward said barrel second end and terminates between said locking aperture and said barrel second end in a second camming surface which opens from said slit portion into a second longitudinal slot portion formed in said longitudinal passage.

12. The combination of claim 11, and in which the barrel second end peripheral surface has an axially-aligned aperture formed therein so as to be in communication with the second longitudinal slot portion to permit the disc stem to pass through the peripheral surface aperture into the longitudinal passage.

13. The combination of any of claims 10, 11 or 12 and in which the longitudinal slot offset opening is offset in the same direction as the disc means threads, whereby threading a cannula onto the disc means will urge the disc stem into the offset opening when the disc means is adjacent the barrel first end.

14. The combination of claim 13, and in which the disc stem terminates in a finger engaging portion having a finger engaging surface extending substantially normal to the disc stem and laterally therefrom so as to be disposed externally of the barrel and generally concentrically with a portion thereof, said finger engaging surface terminating at each of its two lateral extremities in a depending rail portion which engages the barrel peripheral surface, whereby said finger engaging portion is stabilized against said barrel.

*15. In a medical device, the combination of:*

*a cylindrical barrel having a first end and a second end, said second end being open to permit insertion of a container into said second end;*

*disc means transversely disposed within the barrel so as normally to be positioned adjacent to said first end and having an aperture adapted to receive a cannula in axial alignment with the barrel by the engagement of a boss on the cannula with the disc means at the aperture;*

*a longitudinal passage formed in the peripheral surface of said barrel so as to extend parallel to the barrel axis from immediately adjacent the barrel first end through the barrel second end;*

*a stem connected to the disc means within the barrel so as to extend externally of the barrel and generally transverse thereto and operable to initiate longitudinal movement of the disc means relative to the barrel to an operating position adjacent barrel first end, in which, when said cannula is fixed to said disc means, one end of the cannula extends out of the barrel first end, and in which, when the disc means is moved longitudinally away from the barrel first end to a pre-selected disposal position between the barrel second end and the barrel first end, the cannula is completely disposed within the barrel; and*

*locking means for locking the disc means in said disposal position;*

*and in which said longitudinal passage includes a slot portion adjacent the barrel first end and terminating in an offset opening disposed at the first end so that the disc stem can be rotated thereinto when the disc means is adjacent the barrel first end to lock the disc means against longitudinal movement, and a disposal position locking aperture formed in a portion of the longitudinal passage between the barrel second end and the barrel first end in a portion thereof comprised by a longitudinal slit, said slot portion narrowing into said slit portion by means of a first camming surface formed on the barrel between the offset opening and the locking aperture.*

*16. The combination of claim 15, and in which the slit portion of the longitudinal passage extends from said first camming surface through said locking aperture toward said barrel second end and terminates between said locking aperture and said barrel second end in a second camming surface which opens from said slit portion into a second longitudinal slot portion formed in said longitudinal passage.*

*17. The combination of claim 16, and in which the barrel second end peripheral surface has an axially-aligned aperture formed therein so as to be in communication with the second longitudinal slot portion to permit the disc stem to pass through the peripheral surface aperture into the longitudinal passage.*

*18. The combination of any one of claims 15, 16 or 17, and in which*

*the disc means is of a first diameter and the barrel has an interior cross-section which is of a second 5 diameter greater than the first diameter, and*

*the disc stem terminates in a finger engaging portion having a finger engaging surface extending substantially normal to the disc stem and laterally therefrom so as to be disposed externally of the barrel and generally concentrically with a portion thereof, said finger engaging surface terminating at each of its two lateral extremities in a depending rail portion which engages the barrel peripheral surface,*

*whereby said finger engaging portion is stabilized against said barrel so as to suspend the disc means within the barrel by the stem.*

* * * * *